United States Patent [19]

Klein

[11] 4,385,890

[45] May 31, 1983

[54] APPLICATOR TOOL FOR ORTHODONTIC LOOPS

[75] Inventor: Paul E. Klein, Lake Oswego, Oreg.

[73] Assignee: Modcom, Inc., Canby, Oreg.

[21] Appl. No.: 390,299

[22] Filed: Jun. 21, 1982

[51] Int. Cl.³ .............................................. A61C 7/00
[52] U.S. Cl. ..................................................... 433/4
[58] Field of Search .................... 433/3, 4; 221/312 A

[56] References Cited

U.S. PATENT DOCUMENTS

| | | | |
|---|---|---|---|
| 4,001,940 | 1/1977 | Cusato | 433/3 |
| 4,040,187 | 9/1977 | Cardena | 433/3 |
| 4,106,374 | 8/1978 | Dragzn | 433/4 |

Primary Examiner—Robert Peshock

Attorney, Agent, or Firm—Kolisch, Hartwell & Dickinson

[57] ABSTRACT

An applicator tool for use in attaching elastomeric orthodontic loops to orthodontic tooth appliances. The tool includes a pair of pivotal clamping arms having a pair of loop-gripping tips for clamping a loop in a manner permitting attachment of the clamped loop to a tooth appliance. One of the arms has a tapered end portion for holding a stack of such loops for sliding of successive end loops in the stack in a downstream direction. A loop-feed claw mounted on the other arm is adapted first to climb over, and then to engage the upstream side of, an end loop in the loop stack, when the arms are opened, and to place the engaged loop in a position for operative clamping, when the arms are closed.

8 Claims, 6 Drawing Figures

APPLICATOR TOOL FOR ORTHODONTIC LOOPS

BACKGROUND AND SUMMARY OF THE INVENTION

The present invention relates to an applicator tool for use in attaching elastomeric loops to orthodontic tooth appliances.

Typical orthodontic hardware includes metal bands which are mounted, as by cementing, on a person's teeth. Each band has a bracket which receives an archwire used in transmitting desired position-correcting forces. The archwire is fastened to each bracket by a ligature that passes around the archwire and bracket. In recent years, elastomeric loops have become a popular type of ligature for such fastening.

A general object of the present invention is to provide an applicator tool which facilitates dispensing and attaching such elastomeric loops, in a loop-by-loop manner, to a series of tooth appliances.

A more particular object of the invention is to provide such an applicator tool for dispensing and clamping sequentially the end-loops in a stack of loops held on the tool.

The applicator tool of the invention includes a pair of pivotal clamping arms having a pair of loop-gripping tips for clamping an orthodontic loop in a manner permitting attachment of the clamped loop to a tooth appliance. One of the arms is adapted for holding a stack of loops for sliding of successive end loops in a downstream direction, i.e., toward the tip of the arm. A loop-feed claw mounted on the other arm is adapted first to climb over and then to engage the upstream side of an end loop in the stack when the arms are opened, and to place the engaged end loop in a position for clamping when the arms are closed.

These and other objects and features of the present invention will become more fully apparent when the following detailed description of preferred embodiments of the invention is read in connection with the accompanying drawings.

DETAILED DESCRIPTION OF PREFERRED EMBODIMENTS OF THE INVENTION

Figure 1:
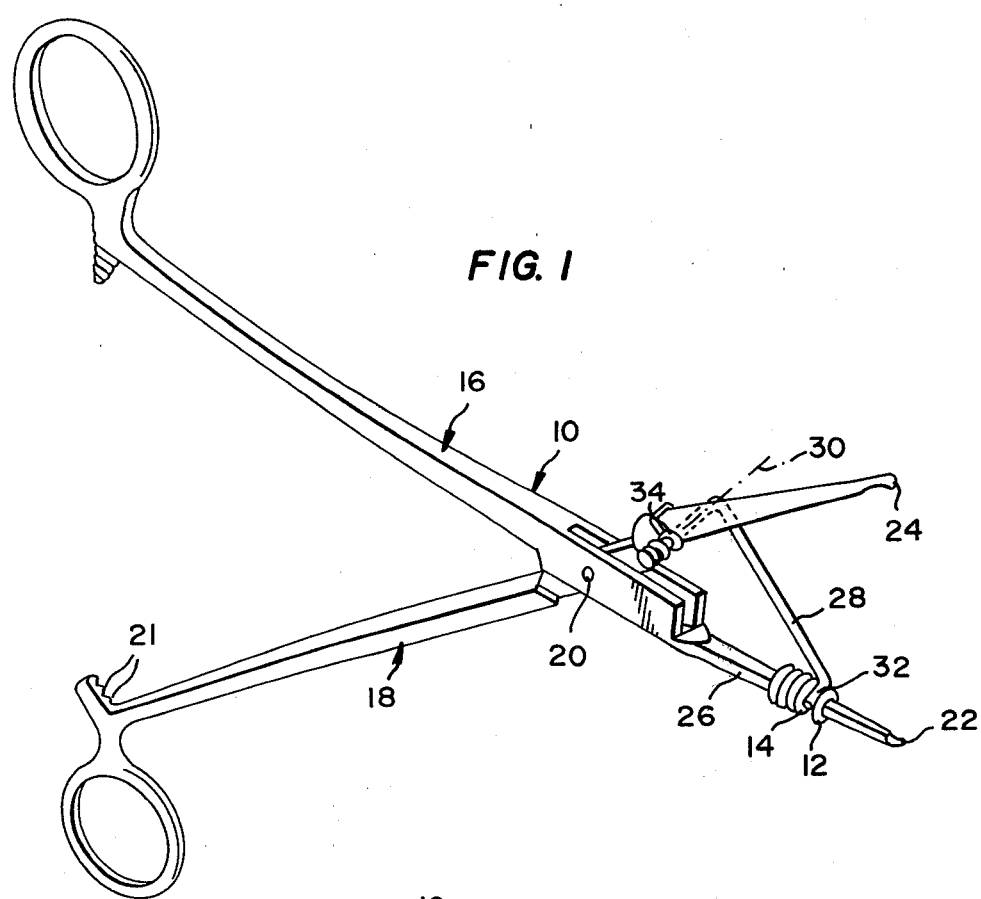
FIG. 1 is a perspective view of an applicator tool constructed according to one embodiment of the invention, shown in an open condition where an end loop in a stack of orthodontic loops is engaged for advancement toward the tip end of the tool.

FIG. 1 shows an applicator tool 10 constructed according to one embodiment of the invention. The tool is designed for use in dispensing a stack of elastomeric orthodontic loops, such as loops 12, 14, and for clamping individually dispensed loops in a manner shown in FIG. 2. Use of the tool will be described below with reference to FIG. 3.

Figure 2:
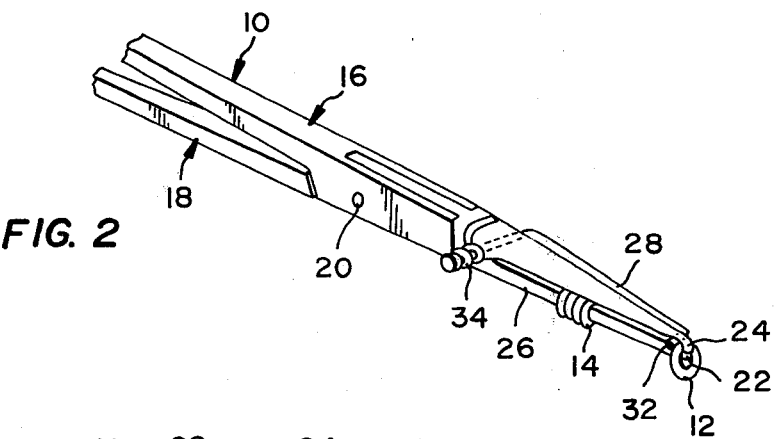
FIG. 2 is an enlarged, fragmentary perspective view of an end portion of the tool of FIG. 1, showing the tool in a closed condition clamping an end loop.

Looking now particularly at FIG. 1, tool 10 has a hemostat-like clamp construction which includes a pair of arms 16, 18 that are pivotally connected at 20 for movement between open and closed conditions, shown respectively in FIGS. 1 and 2. The finger-grip ends of the two arms are each provided with conventional serrated teeth, such as teeth 21 in arm 18, which coact with the teeth in the other arm to produce self locking.

Formed at the other ends of arms 16, 18 are loop-gripping tips 22, 24, respectively, adapted to clamp an orthodontic loop, such as loop 12, in the manner shown in FIG. 2. An end portion 26 in arm 16 is tapered, progressing toward tip 22, for holding a stack of elastomeric loops, such as loops 12, 14, whereby the loops can slide freely on the arm in a downstream direction toward tip 22.

A rigid feed member 28 in the tool is mounted on arm 18 for pivoting about the axis indicated by dash-dot line 30 in FIG. 1. Member 28 is bent at its free end to form a loop-feed claw 32 adapted for engaging and advancing an end loop, such as loop 12, in a manner to be described. A torsion spring 34 operatively interposed between arm 18 and member 28 biases the member in a clockwise direction in FIG. 1 -- that is, in a direction urging claw 32 against the upper surface of portion 26, and in an upstream direction thereon. Thus, as the tool is operated between its open and closed conditions, claw 32 slides in a downstream direction toward tip 22, held at all times firmly against portion 26 by spring 34. Claw 32 is moved toward a downstream position where an end loop, such as loop 12, engaged by claw 32 in the manner shown in FIG. 2, is placed in a position for clamping between tips 22, 24. Spring 34 is also referred to herein as a biasing means, and the spring and member 38 are referred to herein collectively as loop-feed means.

Figure 3:
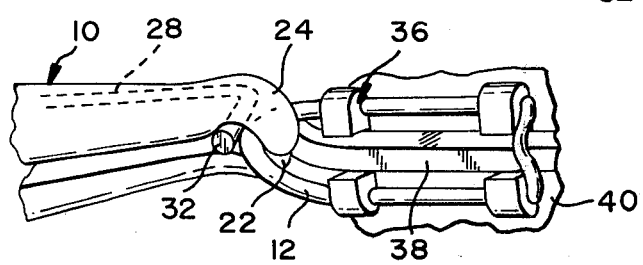
FIG. 3 is an enlarged, fragmentary view of a clamped end loop being attached to an orthodontic tooth appliance.

Tool 10 is constructed for use in dispensing and clamping elastomeric orthodontic loops, to facilitate the ligating of an orthodontic archwire to a series of orthodontic brackets, which are also referred to herein as tooth appliances. FIG. 3 shows a fragmentary portion of a conventional four-post bracket 36, and of an attached archwire 38. Bracket 36 is conventionally mounted on a band, shown fragmentarily at 40, which encircles a tooth to which it is cemented. In the usual case, many of the teeth in the upper and lower jaws are equipped with such band-mounted brackets, and an archwire is constructed to be attached by loop-ligation to each of the upper and lower tooth brackets.

The orthodontist prepares the tool for use by placing a stack of loops on portion 26. The tool is manipulated, to dispense and clamp a loop, first by opening the tool, whereby claw 32 moves in an upstream direction against the upper surface of portion 26 in FIG. 1, toward the end loop in the loop stack. After the claw makes contact with the downstream side of the end loop, the orthodontist continues to open the tool slightly to allow the claw to climb over that loop. The claw then wedges itself, due to biasing by spring 34, between the end loop and the one next to it, engaging the downstream side of the end loop, as shown in FIG. 1. The orthodontist closes the tool to advance the end loop toward tip 22, and to clamp the loop in the manner shown in FIG. 2. With the loop thus clamped, the orthodontist attaches it to a bracket, such as bracket 36, in the manner indicated in FIG. 3. The tool manipulation steps just described are repeated to dispense the loops in the stack in a loop-by-loop manner.

Figure 4:
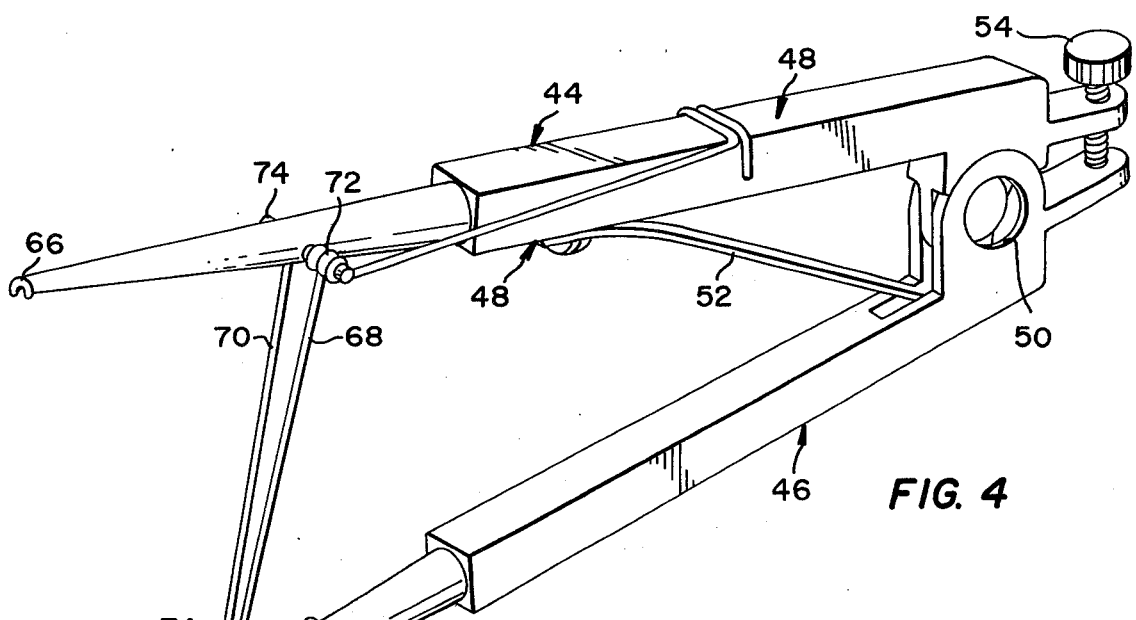
FIG. 4 is a perspective view of an applicator tool constructed according to a second embodiment of the invention, illustrating the manner in which a loop-feed claw in the tool engages an end loop in a stack of loops held on the tool.
Figure 5:
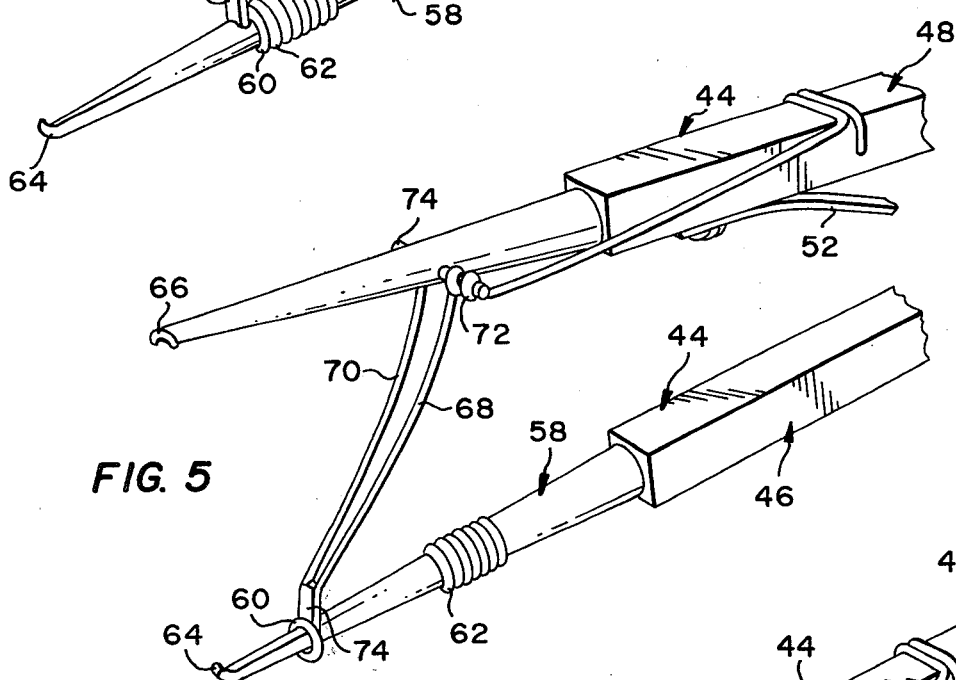
FIG. 5 is a fragmentary view like FIG. 4, but showing an engaged end loop being advanced toward the clamping tips in the tool.
Figure 6:
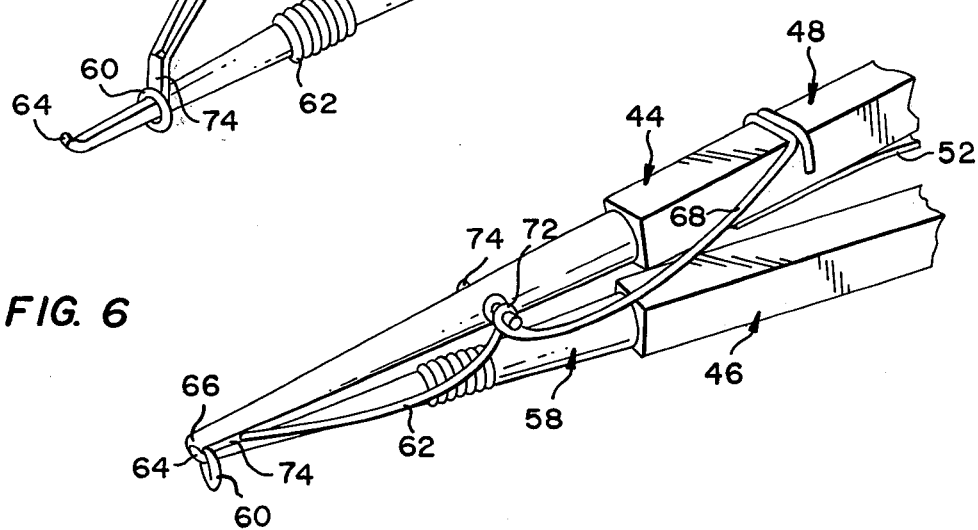
FIG. 6 is a fragmentary view of the tool of FIGS. 4 and 5, shown in a closed condition clamping the end loop.

A second embodiment of an applicator tool is shown generally at 44 in FIGS. 4–6. Tool 44 includes a pair of arms 46, 48 which are pivotally mounted at 50 (see FIG. 4) for movement between an open condition, such as the one shown in FIGS. 4 and 5, and a closed, clamping condition, as shown in FIG. 6. The extent of opening of the tool is limited by a screw-adjustable bolt 54 (FIG. 4) screwed onto arm 48. The arms are biased toward a fully opened condition by a flat spring 52 which is attached to arm 48 and interposed between the two arms.

Arm 46 has an elongated conical loop-holding portion 58 for holding a stack of loops, such as loops 60, 62, along the portion's midregion. Arm 46 terminates, at its left end in the figures, in a loop-gripping tip 64 which is constructed to coact with a half-circle loop-gripping tip 66 formed in arm 48 for clamping a loop in the manner shown in FIG. 6.

Loop-feed means in tool 44 includes two elongate spring members 68, 70 whose coiled midsections, such as midsection 72 in member 68, are held pivotally on opposite sides of a pin 74 carried on arm 48. The right ends of the two members are fashioned to hook over the top of arm 48, thus to anchor the two members on the arm. A loop-feed claw 74 joined to the free ends of the two members is biased against the upper surface of portion 58 in the figures, in an upstream direction, by torsional strain in the two members. The two spring members are also referred to herein as a biasing means.

Use of tool 44 in dispensing and clamping orthodontic loops, in a loop-by-loop manner, is similar to that described above with reference to tool 10. A stack of orthodontic loops, such as loops 60, 62, is placed on portion 58, and the tool is manipulated to produce progressively greater arm opening, to allow claw 74 first to climb over and then to engage the upstream side of the end loop, such as loop 60, in the stack. Here it is noted that bolt 54 can be adjusted periodically to limit the extent of opening of the tool arms to a position just allowing claw 74 to climb over an end loop in the stack. Following such loop engagement, the two arms are closed—causing claw 74 to move downstream (FIG. 5) toward a position placing the engaged loop in a position for clamping between the arm tips (FIG. 6). As can be appreciated particularly with reference to FIG. 6, such downstream claw movement is accommodated by longitudinal bending in the two spring members. It is noted here that while spring members 68, 70 act to urge the two arms toward an open condition, spring 52 provides the principal biasing force which urges the two arms apart.

It can now be appreciated how the present invention, as embodied in tools 10 and 44, facilitates dispensing of elastomeric orthodontic loops, in a loop-by-loop manner, and clamping of loops for ready attachment to an orthodontic bracket of the type described. In particular, both tools described herein allow an orthodontist to place a stack of individual loops on the tool, and then to manipulate the tool in a simple fashion which allows loop dispensing and clamping to be done readily using only one hand.

While preferred embodiments of the invention have been described herein, it will be apparent to those skilled in the art that various changes and modifications can be made without departing from the spirit of the invention.

It is claimed and desired to secure by Letters Patent:

1. An applicator tool for use in attaching elastomeric loops to orthodontic tooth appliances, to secure an archwire thereto, said tool comprising an arm adapted to hold a stack of loops to permit loop sliding in a downstream direction on the arm, another arm mounted for swinging between open and closed positions with respect to the first-mentioned arm, a pair of loop-gripping tips formed adjacent the downstream ends of said arms adapted for clamping a loop, with said other arm in its closed position, in a manner permitting attachment of the clamped loop to a tooth appliance, and loop-feed means mounted on said other arm for sliding contact movement against the first-mentioned arm between an upstream position, where the feed means is adapted first to climb over the downstream side, and subsequently to engage the upstream side, of a loop disposed nearest the tip in said first-mentioned arm, and a downstream position, where the feed means is adapted to place the engaged loop in position for such clamping, when said other arm is moved from said open condition toward said closed position.

2. The tool of claim 1, wherein said feed means includes a loop-feed claw, and biasing means urging said claw against, and in an upstream direction with respect to, said first-mentioned arm.

3. The tool of claim 2, wherein said biasing means includes an elongate spring member acting between said claw and said other arm.

4. The tool of claim 2, wherein said feed means includes a substantially rigid member swingably mounting said claw on said arm, and said biasing means includes a torsion spring biasing said rigid member in a direction which urges the claw thereon against, and in an upstream direction with respect to, said first-mentioned arm.

5. The tool of claim 1, wherein said first-mentioned arm includes a loop-holding portion which is tapered convergently progressing toward the tip end of said arm.

6. An applicator tool for use in attaching elastomeric loops to orthodontic tooth appliances, to secure an archwire thereto, said tool comprising a pair of arms pivotally connected for movement toward and away from each other between closed and open conditions, respectively, a pair of loop-gripping tips formed adjacent the arm ends for clamping a loop, with the arms closed, in a manner permitting attachment of the clamped loop to a tooth appliance, one of said arms including an end portion which is tapered convergently progressing toward the associated arm tip for holding a stack of loops for sliding on said portion in a downstream direction toward said tip, a loop-feed claw mounted on the other of said arms for sliding-contact movement against the tapered portion in said one arm between an upstream position, where the claw is adapted first to climb over the downstream side, and then to engage the upstream side, of a loop disposed nearest to the tip on the tapered portion in the one arm, and a downstream position where the claw is adapted to place the engaged loop in position for such clamping, when the arms are moved from said open condition toward said closed condition, and biasing means on said other arm urging said claw against, and in an upstream direction with respect to, said one arm portion.

7. The tool of claim 6, wherein said biasing means includes an elongate spring member acting between said claw and said other arm.

8. The tool of claim 6, which further includes a substantially rigid member swingably mounting said claw on said other arm, and said biasing means includes a torsion spring biasing said rigid member in a direction which urges said claw against, and in an upstream direction with respect to, said one arm portion.

* * * * *